United States Patent [19]

Stangeland

[11] Patent Number: 4,674,322
[45] Date of Patent: Jun. 23, 1987

[54] ON-LINE INSTRUMENT FOR SIMULTANEOUSLY MEASURING THE VISCOSITY, DENSITY, AND SURFACE TENSION OF A FLUID COMPRISING A GAS DISSOLVED IN A LIQUID

[75] Inventor: Bruce E. Stangeland, Berkeley, Calif.

[73] Assignee: Chevron Research Company, San Francisco, Calif.

[21] Appl. No.: 796,037

[22] Filed: Nov. 7, 1985

Related U.S. Application Data

[63] Continuation-in-part of Ser. No. 664,895, Oct. 25, 1984, abandoned.

[51] Int. Cl.$^4$ ............................................. G01N 11/10
[52] U.S. Cl. ........................................ 73/54; 73/64.4; 73/32 R
[58] Field of Search ................... 73/59, 54, 64.4, 32 R

[56] References Cited

U.S. PATENT DOCUMENTS

| | | | |
|---|---|---|---|
| 3,382,706 | 5/1968 | Fitzgerald | 73/59 |
| 3,808,893 | 5/1974 | Jinno et al. | 73/61.1 R |
| 3,926,037 | 12/1975 | Kopito et al. | 73/64.4 |
| 4,148,215 | 4/1979 | Hofstetter, Jr. | 73/54 |
| 4,226,798 | 10/1980 | Cowfer et al. | 73/54 |
| 4,437,337 | 3/1984 | Fenrick | 73/54 |
| 4,466,276 | 8/1984 | Ruyak et al. | 73/59 |

FOREIGN PATENT DOCUMENTS

| | | | |
|---|---|---|---|
| 15837 | 1/1984 | Japan | 73/54 |
| 685958 | 9/1979 | U.S.S.R. | 73/54 |
| 756277 | 8/1980 | U.S.S.R. | 73/54 |
| 935744 | 6/1982 | U.S.S.R. | 73/32 R |

OTHER PUBLICATIONS

Nissen, A Single Apparatus for the Precise Measurement of the Physical Properties of Liquids at Elevated Temp. & Pressure, unlimited release, 10-1980.

Primary Examiner—Stewart J. Levy
Assistant Examiner—Hezron E. Williams
Attorney, Agent, or Firm—S. R. La Paglia; W. K. Turner; T. G. DeJonghe

[57] ABSTRACT

An instrument for simultaneously measuring the viscosity, density, and surface tension of a fluid comprising a gas dissolved in a liquid, at the operating conditions of the fluid, employing an instrument based on the principle of a damped, one-dimensional harmonic oscillator; the instrument being adapted to receive the fluid on-line without altering its operating environment.

11 Claims, 1 Drawing Figure

U.S. Patent  Jun. 23, 1987  4,674,322
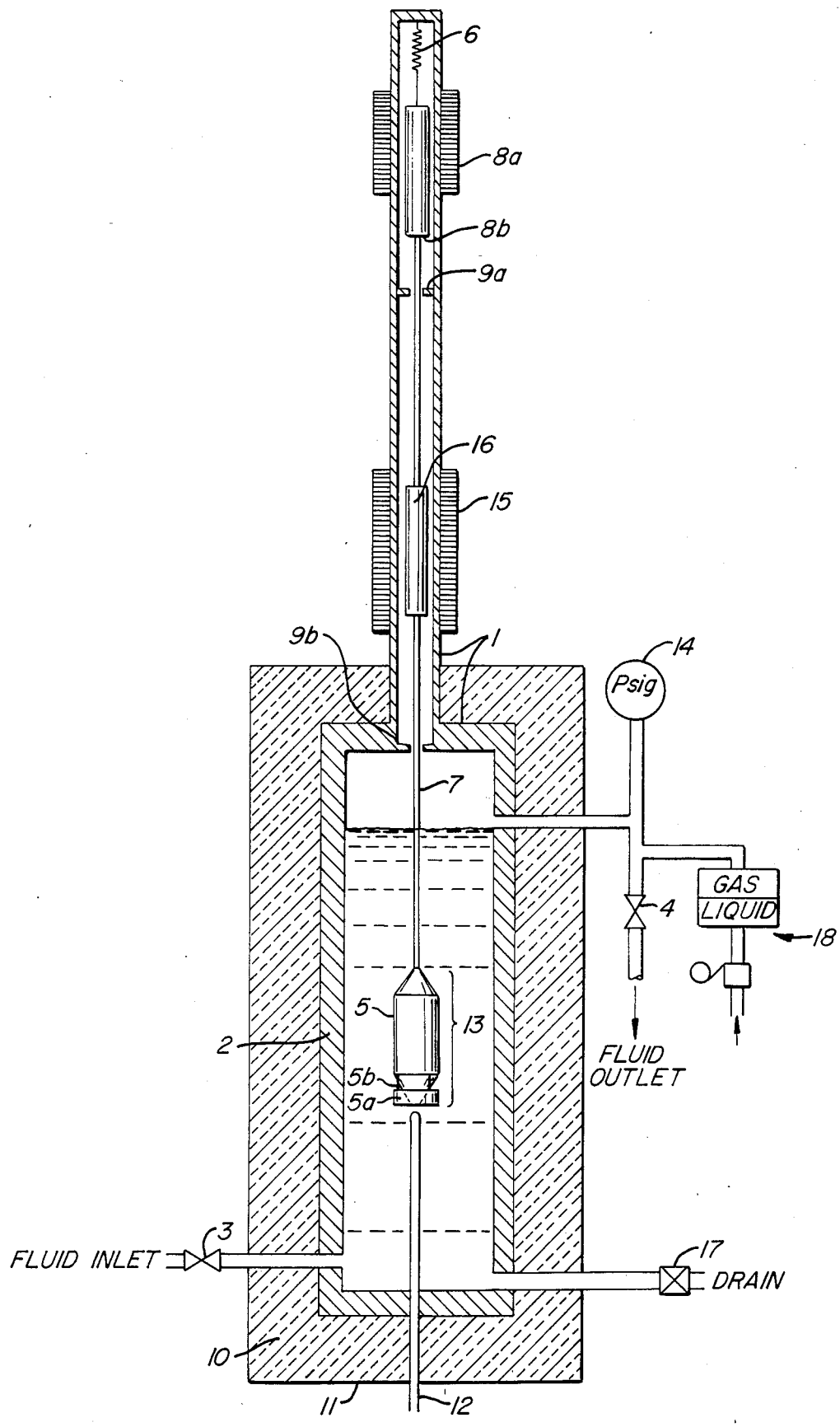

ON-LINE INSTRUMENT FOR SIMULTANEOUSLY MEASURING THE VISCOSITY, DENSITY, AND SURFACE TENSION OF A FLUID COMPRISING A GAS DISSOLVED IN A LIQUID

CROSS-REFERENCE TO RELATED APPLICATIONS

This application is a continuation-in-part of U.S. patent application Ser. No. 664,895, filed Oct. 25, 1984, now abandoned.

BACKGROUND OF THE INVENTION

This invention relates to an on-line instrument which simultaneously measures the viscosity, density, and surface tension of fluids in their operating environment. It is based upon the principle of a damped, one-dimensional harmonic oscillator, and is specifically adapted for use when measuring the physical properties of fluids comprising a gas dissolved in a liquid. In particular, the instrument of this invention will accurately and simultaneously measure the operating density, viscosity, and surface tension of such fluids.

Knowing the physical properties of fluids, such as density, viscosity (as either the dynamic or kinematic viscosity), and surface tension, is essential when designing fluid handling equipment. Yet these properties vary to a considerable degree depending upon the precise operating conditions which the fluid encounters. In particular, the successful design and operation of refinery processing units depend on a knowledge of the physical properties of the process fluids at operating conditions. It is frequently difficult to obtain such data. Thus, physical properties, such as viscosity, density, and surface tension, are extrapolated from measurements made at much less severe conditions. Such extrapolations, however, interject error into design and operating calculations and create deficiencies in the refinery processing units.

For example, inaccurately calculated physical properties can lead to nonuniform temperature and flow distributions throughout fixed-bed reactors. This creates hot spots in the reactor and results in reduced product yields. To alleviate this situation, an instrument is needed that can measure physical properties up to 800° F. and 3000 psia. Further, such an instrument must be capable of reproducing the precise environment encountered by the fluid in order to provide accurate measurements.

Fluids which comprise a gas dissolved in a liquid present an additional burden. The physical properties of these fluids depend upon the concentration of the gas in the liquid, which in turn depends upon the operating environment encountered at the time the fluid is formed. Removing the fluid from that environment may alter its physical properties. Of particular importance is the measure of viscosity.

Conventional instruments measure viscosity as either the ratio of an applied stress, such as gravity, to the resulting velocity, or, as the time required for a given volume of fluid to flow through a capillary or restriction. When viscosity is measured as the ratio of applied stress to resulting velocity it is referred to as absolute or dynamic viscosity and is measured in units called "poise" with the dimensions dyne-sec/cm$^2$. When viscosity is measured as the flow rate of the fluid, it is referred to as kinematic viscosity. Kinematic viscosity is also the ratio of the dynamic viscosity to the density of the fluid and in the cgs system is measured in units called "stokes" with the dimensions cm$^2$/sec.

Viscometers generally fall into fundamental groups depending upon the measurement they take: those which measure kinematic viscosity, such as capillary viscometers; and those which measure dynamic viscosity, such as rotational viscometers, falling body viscometers, and oscillational viscometers.

Oscillational viscometers offer a number of desirable features and are useful over a wide range of viscosities. They are based on the relationship between the amplitude of the oscillations of an object oscillating in the fluid and the viscosity of the fluid. This relationship imposes restrictive experimental conditions on the use of oscillational viscometers so that they are not generally suited for use at elevated temperatures and pressures. Sandia National Laboratories ("Sandia") has, however, reported the development of an improved one-dimensional oscillational viscometer which overcomes certain of the restrictions encountered when measuring viscosity at elevated temperatures or pressures by measuring the rate of damping of an oscillating immersed plate suspended from a helical spring [Sandia National Laboratories (SAND 80-8034) Unlimited Release Printed October 1980, "A Single Apparatus For the Precise Measurement of the Physical Properties of Liquids at Elevated Temperature and Pressure", D. A. Nissen].

Despite advantages, the instrument reported by Sandia and similar instruments do not overcome the problems encountered when it is desirable to know the physical properties of fluids comprising a gas dissolved in a liquid. In order to employ conventional off-line oscillational viscometers, a fluid sample is placed in the instrument, and equilibrated at elevated temperature and pressure. Since the sample is brought to its operating conditions in the instrument outside of its operating environment, if the fluid comprises a gas dissolved in a liquid, the fluid sample may not represent the fluid in its operating environment. If the fluid sample is not representative of the fluid in its operating environment, conventional off-line instruments are ineffective.

Accordingly, an instrument which can be used to determine the physical properties such as density, viscosity, and surface tension of fluids comprising a gas dissolved in a liquid at elevated temperatures and pressures would be advantageous. It is the principle object of this invention to provide such an instrument.

Furthermore, instruments such as the one reported by Sandia are incapable of simultaneous measurement of viscosity, density, and surface tension. For example, Sandia's instrument is incapable of measuring viscosity and density with a single float. A thin plate is used to measure viscosity and surface tension but a larger volume bob is required to determine density. The change in equipment interjects error into the measurement and requires two separate samples, resulting in further possibility of error.

It is, therefore, highly desirable to have an instrument that can simultaneously measure viscosity, density, and surface tension, at elevated temperatures and pressures. It is a further object of this invention to provide such an instrument.

SUMMARY OF THE INVENTION

The viscosity, density, and surface tension of a fluid comprising a gas dissolved in a liquid can be accurately and simultaneously measured by the instrument encompassed by this invention. Further, the instrument is adapted for on-line use.

The instrument comprises a housing which encloses a sealable chamber having an inlet opening through the housing fitted to receive fluid directly from its operating environment under its operating conditions and to discharge fluid from the chamber. Located within the chamber is a pendulous one-dimensional oscillational assembly having an immersible oscillatory pendant object, and a means for initiating free oscillations of the object while immersed in fluid within the chamber. In addition, the chamber has a means for controlling the temperature and pressure of the environment within the chamber.

The pendant object has a cone-shaped top and bottom and a cylindrical skirt, circumscribing the bottom of the object and comprising a means for the escape of entrained gas bubbles. The cylindrical skirt provides a fixed perimeter for the measurement of surface tension; the tapered top and bottom of the object permit proper drainage of the fluid and provides a measurement of viscosity; and the object displaces the necessary volume for measurement of density. These features combine to provide simultaneous and accurate measurement of density, viscosity, and surface tension.

In a preferred embodiment, the pendulous oscillational assembly includes a pendant object affixed to a helical spring suspended within the chamber which is in tension when the pendant object is at rest. The assembly is associated with (i) means for remotely initiating oscillations of the spring to freely oscillate the affixed pendant object immersed in the fluid which damps the oscillations until the pendant object returns to rest; and (ii) means for measuring and recording the characteristic at rest position of the pendant object immersed in the fluid, the amplitude of each oscillation of the pendant object, and the change in position of the object because of the downward force exerted on the pendant object as it is separated from the fluid just prior to breaking free from the fluid.

BRIEF DESCRIPTION OF THE DRAWING

This invention is described in greater detail below by referring to a preferred embodiment schematically shown in the accompanying FIG. 1 illustrating in a longitudinal sectional view an instrument contemplated by this invention.

DETAILED DESCRIPTION OF THE INVENTION

The instrument illustrated in FIG. 1 comprises a housing 1 enclosing a sealable chamber 2 with valved inlet opening 3 associated with an appropriate fitting to allow a direct connection between the operating environment of the fluid and sealable chamber 2. Although the fitting is an essential element of the invention, its features depend upon the location of the fluid. Generally, the fluid will be confined within a high pressure vessel and fittings such as those employed by conventional high pressure sampling bombs are suitable. Similarly, chamber 2 has valved outlet opening 4 as a fluid discharge port.

Pendant object 5 is located within chamber 2 and is affixed by means of lifting and centering rod 7 to helical spring 6 which is in turn suspended within chamber 2. Object 5 possesses a cone-shaped top and bottom which allow drainage of the fluid. Cylindrical skirt 5a encompassing, and attached to object 5 by a plurality of vertical support members 5b provides a fixed perimeter, allowing for the accurate measurement of surface tension. In addition, any entrained gas bubbles pass out between the vertical support members and escape into the surrounding fluid.

Stainless steel springs are typically employed in linear oscillational viscometers since they obey Hooke's Law at reasonable extensions and are relatively unaffected by temperature changes. When pendant object 5 is in its raised position (as illustrated) the tension on spring 6 is reduced and object 5 remains below the fluid level established by outlet opening 4. In this manner, when object 5 is released, it remains immersed in the fluid over the full range of its oscillations through the fluid. In the illustrated embodiment, object 5 is raised and held in place by the action of lifting magnet 8a on the ferromagnetic core 8b. When released, object 5 will descend over a linear path governed by centering rod 7 and centering guides 9a and 9b until helical spring 6 has been extended and begins to return to its initial position, thus oscillating object 5 through the fluid. Ideally, housing 1 will be mounted precisely enough so that the centering rod 7 will not rub against the centering guides 9a and 9b. Rubbing against these guides would introduce a friction factor into the calculations required to measure the properties of the fluid and thus complicate the use of this instrument.

In the instrument illustrated in FIG. 1, temperature stability and control are achieved by an insulating jacket 10 covering housing 1, and heating coils 11. Heating coils 11 are positioned relative to housing 1 to insure that the fluid exhibits a uniform temperature, especially across zone 13 of the fluid through which object 5 will oscillate. Thermowell 12 is located to accurately measure the temperature in zone 13 and to provide feedback control to heating coils 11. Pressure is either determined by the pressure of the operating environment of the system to which the instrument is attached via inlet opening 3, or it is controlled by adjusting a gas source using pump and pressurizing system 18 interconnected to chamber 2 via outlet opening 4 and is measured by pressure gauge 14. In the event that a gas source is used to pressurize chamber 2 when using the instrument to measure the physical properties of a fluid comprising a gas dissolved in a liquid, it is essential that the source gas and pressure be selected and controlled to avoid changing the solubility of the gas constituent of the fluid or driving the source gas into solution. Suitable pump and pressurizing systems are commercially available. For example, Brownlee Model G Gradient Dual Pump System is an acceptable commercially available system.

A commercially available linear variable differential transformer 15 is used as a position transducer to measure the amplitude of the oscillations and the at-rest position of pendant object 5. This device delivers an electrical signal whose magnitude is directly proportional to the elevation of the ferromagnetic core 16 within the surrounding core.

It will be evident to those familiar with such instruments that this invention contemplates numerous embodiments comprising various pendant objects having a fixed perimeter, and means for on-line connection, oscillating the pendant object, recording the amplitude of oscillations, the at-rest position of the pendant object, and controlling temperature and/or pressure. The essential features of the present invention reside in the unique combination of these elements in an instrument designed for on-line use, not in the specific means selected for each feature.

It is also evident that to achieve the benefits of this invention, it is essential that the instrument must be calibrated to account for mechanical characteristics, such as frictional influences, spring constants, and similar factors affecting oscillation of the object through the fluid (referred to as "instrument constants"), and periodically, the instrument must be tested against standards and if necessary, re-calibrated. D. A. Nissen's publication, previously mentioned, details the theory and calibration of one-dimensional oscillational viscometers and is incorporated herein by reference. In general, linear oscillational viscometers are calibrated as follows: after an initial lineout period of several cycles, the amplitude of the oscillations will decay exponentially, that is, a plot of the log of the amplitude versus cycle number will give a straight line. The slope of this line, called the logarithmic decrement, can be defined as $$\sigma = \frac{1}{n} \cdot \text{Ln}\left(\frac{\text{Amplitude of cycle } o}{\text{Amplitude of cycle } n}\right)$$

The fluid properties are related to $\sigma$ by the following equation $$\sqrt{\eta \cdot \rho} = C_1 \cdot \sigma + C_2,$$

where $C_1$ and $C_2$ are instrument constants and $\eta$ and $\rho$ are the viscosity and density of the fluid, respectively.

Thus, the instrument is calibrated by plotting $\sqrt{\eta \cdot \rho}$ vs $\sigma$ for known fluids.

A principle advantage of the instrument of this invention resides in its ability to measure the physical properties of select fluids, which because of the conditions encountered in their operating environment, comprise a gas or gases dissolved in a liquid or liquids, i.e., single-phase mixtures in their operating environment and multiple phase mixtures at ambient conditions. As previously noted, conventional one-dimensional oscillational viscometers are limited to measuring the physical properties of fluids which can be sampled without altering their phase or, consequently, without altering their physical properties. Fluids which because of their operating environment comprise, at their operating conditions, a gas dissolved in a liquid generally cannot be sampled in this xanner. The ability to use the instrument of this invention to measure the physical properties of such fluids is attributable to its adaptation to on-line use. In particular, the sealable chamber and fitted inlet characteristic of the instrument maintain the operating environment of the fluid so that physical properties of the fluid in its operating environment can be measured. Thus, the physical properties at elevated temperature and/or pressure of a wide variety of fluids can be determined using the instrument of this invention. The single-phase gas-liquid fluids typical of fluids whose physical properties are measured using the instrument of this invention are relatively common in the petroleum industry where hydrocarbon processing units are typically designed to handle liquid petroleum products containing dissolved gases such as hydrogen, light hydrocarbons, hydrogen sulfide, and the like.

A further advantage of the invention is the structure of the pendant object which comprises a means that allows drainage of the fluid and escape of the dissolved gas. In the illustrated embodiment, the vertical members which fix the cylindrical skirt to the pendant object are spaced sufficiently apart to allow for escape of gas bubbles. Various other means, such as apertures in the skirt, could be employed. The pendant object also comprises a tapered top and bottom. This design allows drainage and prevents the trapping of fluid within the pendant object. Thus, the pendant object passes through the fluid uninhibited, allowing for accurate measurement of viscosity, density, and surface tension.

Another advantage of the invention resides in its ability to simultaneously measure the density, viscosity, and surface tension of fluids. The pendant object comprises unique features that provide accurate measurement of each property. As noted above, the object must possess a fixed perimeter to accurately measure surface tension. The cylindrical skirt provides such a perimeter. In addition, the measurement of surface tension requires uninhibited drainage from around the object. This is provided by the object's tapered top and bottom. Also, the object displaces the necessary volume of fluid to accurately measure density. Further, density measurements are not distorted by the presence of entrained gas because the gas escapes through the open areas between the vertical support members which support the cylindrical skirt. In sum, the single pendant object measures all pertinent physical properties of the fluid, dispensing with the need to change equipment during measurement. Thus, the instrument maintains a constant operating environment, eliminating the introduction of error that a change in equipment would produce.

The instrument illustrated in FIG. 1 is operated by equilibrating chamber 2 at the desired temperature and pressure, while admitting fluid through inlet opening 3 until the fluid level rises to a fixed point above the level to which object 5 will be raised, and sealing chamber 2. Typically, this level would be the point at which excess fluid reaches the outlet and begins flowing out the fluid outlet 4.

The position of object 5 at rest reflects a balance between gravity pulling down and of two upwardly acting forces: the tension in spring 6 and the buoyancy exerted on object 5 by the fluid. Denser fluids will exert more buoyancy force, so the rest position of the object will be higher. The density of any fluid can thus be determined by comparing the rest position of object 5 in the fluid with the at-rest position for known standards.

Object 5 is then lifted to its raised position by engaging lifting magnet 8a. Disengaging lifting magnet 8a will initiate oscillations. The amplitudes of the resulting oscillations of object 5 in the fluid are recorded. The rate of damping the oscillations of object 5 is characteristic of a given fluid. By comparing this decay in amplitude of the oscillations of object 5 to known standards, the viscosity of the fluid can be measured.

Surface tension is measured by slowly and continuously separating the fluid and the pendant object immersed in it, and measuring the maximum force exerted on the object (which occurs just prior to the point in time when the object breaks free from the fluid). The surface tension of the fluid can then be calculated by the formula $$\gamma = \frac{F}{P \cos \theta}$$

where $\gamma$ is the surface tension, F is the maximum force exerted on the object, P is the perimeter of the object, and $\theta$ is the wetting angle that is generally assumed to be zero if the fluid wets the object. In order to accurately establish the perimeter of the pendant object, the shape of the object should be such as to provide a fixed perimeter. Thus, the pendant object comprises a cylindrical skirt having a fixed perimeter. Other configurations, such as a sphere, although suitable for measuring viscosity or density, are not generally suited for surface tension measurements since their perimeters vary as the fluid is drained from around them.

Referring again to the instrument illustrated in FIG. 1, the fluid is separated from the object by draining the fluid from chamber 2 through valved drain 17. In this way, the rate of separation is controlled by the valve and can be carefully controlled while measuring the change in position of object 5. The maximum force exerted on the object, F in the above formula, is detected as an apparent increase in the weight of the object and is measured as a change in position of the object, i.e., the object moves downward. According to Hooke's Law the force exerted on the object is a function of the linear change in position of the object for a given spring. Thus, it is possible to correlate the change in position of the object to the force exerted on the object. Accordingly, surface tension can be calculated using the above formula where F is determined by its correlation to the change in position of the object. Furthermore, since according to the above formula surface tension is directly related to the force exerted on the object for a given instrument, the linear change in position of the object can be directly correlated to surface tension. In this manner, the surface tension may be determined directly by calibrating the instrument against known standards. In order to determine the accuracy of surface tension measurements made with the instrument, it is desirable to measure the surface tension of a fluid having a known surface tension and compare the results with the known values.

The following claims define the scope of the invention just detailed.

What is claimed is:

1. A linear oscillational instrument used to measure the viscosity, density, and surface tension of a fluid having at least one gas dissolved in a liquid comprising a housing enclosing a sealable chamber having an opening through which said fluid may be directly received from its operating environment and discharged from said chamber, said chamber:
   (a) having suspended therein a pendulous linear oscillational assembly including an immersible pendant object having a structure which:
     (1) comprises a tapered top and bottom and allows uninhibited drainage of fluid from said object, and
     (2) provides a fixed perimeter cylindrical skirt attached to the base of said tapered bottom so as to produce a plurality of apertures spaced about said object, which apertures will allow the escape of entrained gas bubbles, and said pendulous oscillational assembly having a means for initiating oscillations of said object while immersed in said fluid within said chamber; and
   (b) having associated therewith means for controlling the temperature and pressure of the environment within said chamber.

2. An instrument according to claim 1 wherein said pendant object comprises:
   (1) a cone-shaped top; and
   (2) a cone-shaped bottom.

3. An instrument according to claim 4 wherein said pendant object comprises a cone-shaped top and bottom which allow uninhibited drainage of fluid from said object.

4. An instrument according to claim 1 wherein said pendulous assembly comprises said pendant object affixed to a helical spring suspended within said chamber and in tension when said pendant object is at rest, said assembly being associated with and functioning in cooperation with a means for remotely initiating oscillations of said spring to oscillate said affixed pendant object through said fluid.

5. An instrument according to claim 4 wherein said means for initiating oscillations comprises a lifting magnet acting upon said pendulous assembly when engaged so as to lift said pendant object to a raised position and maintain said object in said raised position until subsequently disengaged allowing said object to descend and initiate linear oscillations of said spring dampened by the action of said fluid on said pendant object until said object comes to rest.

6. An instrument according to claim 1 wherein said means for elevating and controlling the temperature of the environment within said chamber comprises heating coils enclosed in an insulating jacket about said housing.

7. An instrument according to claim 1 wherein said means for elevating and controlling the pressure of the environment within said chamber comprises a pump and pressurizing system interconnected to said chamber above the fluid level thereof.

8. An instrument according to claim 4 wherein said spring is a helical metallic spring 9. An instrument according to claim 8 wherein said spring is a helical stainless steel or bronze spring.

10. An instrument according to claim 8 wherein said spring is a helical quartz spring.

11. A method for determining simultaneously the viscosity, density, and surface tension of a fluid comprising a liquid component and a gas component at a temperature and pressure sufficient to maintain said gas component dissolved in said liquid component, comprising the steps of:
   (1) introducing said fluid into the sealable chamber of the instrument defined according to claim 1 at least until said fluid is sufficient to submerse said object during oscillation;
   (2) maintaining the environment of the sealable chamber at the operating conditions of said fluid at which its density, viscosity, and surface tension are to be measured;
   (3) comparing the at-rest position of said object in said fluid to known standard to determine the density of said fluid;
   (4) initiating oscillations of said object in said fluid;
   (5) measuring the amplitudes of said oscillations;
   (6) comparing the logarithmic decrement of the oscillation decay curve for said oscillations at said temperature and pressure to known standards to determine the viscosity of said fluid;
   (7) separating said fluid from said object;
   (8) measuring the change in said object's position during said separation; and
   (9) comparing the change in position of said object to known standards to determine the surface tension of the fluid.

* * * * *